United States Patent
Fischell

(10) Patent No.: US 9,204,988 B1
(45) Date of Patent: Dec. 8, 2015

(54) NASAL STRIP HAVING IMPROVED CHARACTERISTICS

(71) Applicant: Robert E. Fischell, Dayton, MD (US)

(72) Inventor: Robert E. Fischell, Dayton, MD (US)

( * ) Notice: Subject to any disclaimer, the term of this patent is extended or adjusted under 35 U.S.C. 154(b) by 0 days.

(21) Appl. No.: 14/468,881

(22) Filed: Aug. 26, 2014

(51) Int. Cl.
*A61F 5/08* (2006.01)

(52) U.S. Cl.
CPC ........................... *A61F 5/08* (2013.01)

(58) Field of Classification Search
CPC .............. A61F 5/56; A61F 5/08; A61B 1/233
USPC ............................................. 606/199, 204.45
See application file for complete search history.

(56) References Cited

U.S. PATENT DOCUMENTS

2013/0197569 A1* 8/2013 Allen ....................... 606/204.45

* cited by examiner

*Primary Examiner* — Victor Nguyen
(74) *Attorney, Agent, or Firm* — Rosenberg, Klein & Lee

(57) ABSTRACT

A nasal strip having a non-adhesive central portion situated between two adhesive end sections of the nasal strip. In one example, a thin plastic covering over the adhesive surface of the central portion of the nasal strip provides advantages of more torque obtained to open the nasal passageways, less discomfort on removal of the nasal strip, easier placement of the nasal strip onto the nose and less area of the skin on the nose that can be irritated by the adhesive interior surface of the nasal strip.

6 Claims, 1 Drawing Sheet

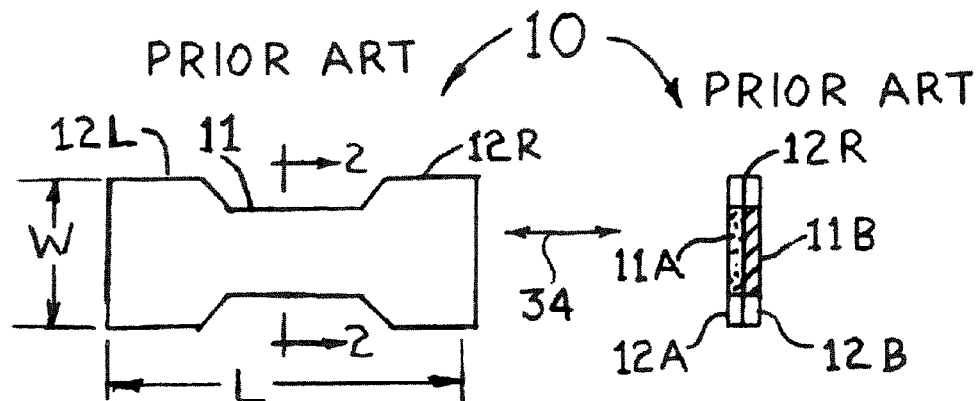
FIG. 1 FIG. 2
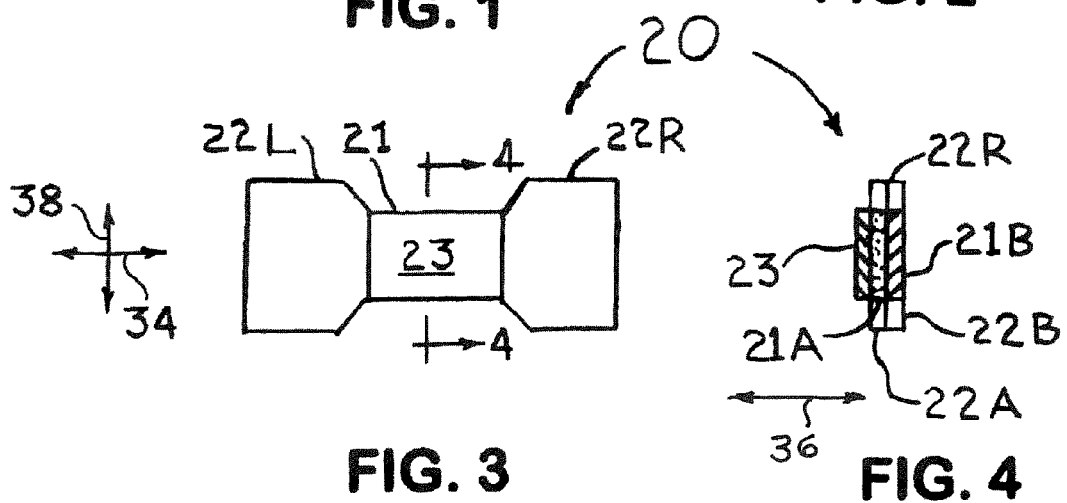
FIG. 3 FIG. 4
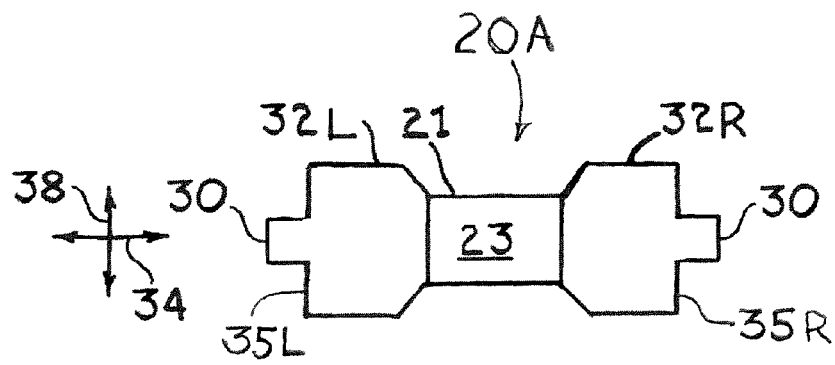
FIG. 5

NASAL STRIP HAVING IMPROVED CHARACTERISTICS

FIELD OF USE

This invention is in the field of devices to improve the opening of the nasal passageways.

BACKGROUND OF THE INVENTION

It is well known to use adhesive strips attached to the skin across the outside of the nose to improve the opening of the nasal passageways, particularly during sleep. One example of such a device is the Breathe Right nasal strip which is a product of GlaxoSmithKline. However, that device has the disadvantage of only applying a moderate torque for opening the nasal passage and also, the adhesive attachment to the skin is so strong that there is some discomfort when that nasal strip is removed from the nose. Still further, there is sometimes an irritation of the skin on the nose when this nasal strip is repeatedly used for many consecutive days or night.

Therefore, any nasal strip that could have: 1) more torque applied to open the nasal passageway, 2) less discomfort when the nasal strip is removed, 3) easier means for holding the nasal strip for placement onto the nose, and 4) a decrease in the area of the skin that could be irritated by the adhesive attached to the skin would all constitute improvements in the design of such devices.

SUMMARY OF THE INVENTION

The present invention is a novel and useful means to improve the characteristics of nasal strips by the placement of a non-adhesive central portion situated between the two adhesive end sections of the nasal strip. For example, a thin plastic covering over the adhesive surface of the central portion of a nasal strip can provide the four advantages of more torque obtained to open the nasal passageway, less discomfort on removal of the nasal strip, easier means for placement of the nasal strip onto the nose and less area of the skin on the nose that can be irritated by the adhesive interior surface of the nasal strip.

Thus one object of the present invention is to increase the torque applied by a nasal strip to improve the opening of the nasal passageways.

Another object of this invention is to decrease the user's discomfort when removing the nasal strip from his/her nose.

Still another object of this invention is to have a central region of the nasal strip that does not have an adhesive surface so that it is more easily held when placing the nasal strip onto the nose.

Still another object of this invention is decrease the area of the skin that can be irritated by the application of the nasal strip for many hours, particularly during sleep.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 1 is a plan view of a prior art nasal strip;

FIG. 2 is a cross section of the nasal strip at section "2-2" of FIG. 1 showing the positions of the adhesive surfaces and the plastic backing of the prior art nasal strip;

FIG. 3 is a plan view of the present invention showing a non-adhesive covering of the central portion of the nasal strip;

FIG. 4 is a cross section of the present invention at section "4-4" of FIG. 3 showing a plastic covering over the adhesive surface at the central portion of the improved nasal strip; and, FIG. 5 is a plan view of the present invention showing a non-adhesive tab member secured to a boundary of a right section and/or a left section of the nasal strip.

DETAILED DESCRIPTION OF THE INVENTION

FIG. 1 is a plan view of a typical prior art nasal strip 10 that is used to provide improved openings of the nasal passageways particularly during sleep. The nasal strip 10 has a central portion 11, a right section 12R, and a left section 12L. A typical nasal strip 10 has a length "L" that is approximately 6 cm and a maximum width "W" that is approximately 2 cm with a length of the central portion 11 being about 2.5 cm.

FIG. 2 is a cross section of the nasal strip 10 at section "2-2" of FIG. 1. The central portion 11 of the nasal strip 10 would have a back portion 11B and an interior surface that would have an adhesive covering 11A. The right section 12R would have a back portion 12B and an interior adhesive covering 12A. The entire external portion of the nasal strip 10 would be formed from a flexible plastic material like that used for skin bandages. The entire interior surface of the nasal strip 10 would have an adhesive covering so that it would adhere to all parts of the skin on the nose onto which it would be placed.

FIG. 3 is a plan view of the present invention which is a nasal strip 20 that is an improved device to provide an opening of the nasal passageways particularly during sleep. The nasal strip 20 has a central portion 21 that has an interior covering 23, a right section 22R, and a left section 22L. This nasal strip 20 would also have a length that is approximately 6 cm, a maximum width "W" that is approximately 2 cm, and a length of the central portion 21 that is approximately 2.5 cm.

FIG. 4 is a cross section of the nasal strip 20 at section "4-4" of FIG. 3. The central portion 21 of the nasal strip 20 would have a back portion 21B and its central portion 21 would have a centrally located adhesive covering 21A onto which the interior covering 23 is attached. The right section 22R would have a back portion 22B and an interior adhesive covering 22A. The entire external portion of the nasal strip 10 would be formed from a flexible plastic material like that used for skin bandages. Unlike the prior art design as shown in FIGS. 1 and 2, the interior surface of the nasal strip 20 would not have an adhesive covering throughout its entire interior surface. For this improved design of the nasal strip 20, the central portion 21 would have the plastic covering 23 on its interior surface as is shown in FIGS. 3 and 4. This plastic covering 23 would adhere to the adhesive covering 21A of the central portion 21 of the nasal strip 20. It should also be understood that the present invention includes the concept of eliminating the coating on the central portion 21 without having the interior covering 23. This alternative design would provide several advantages of the present invention but not the increased torque that is a feature of the design of FIGS. 3 and 4.

There are four improvements in the design of the nasal strip 20 of FIGS. 3 and 4 as compared to the prior art nasal strip 10 of FIGS. 1 and 2. Firstly, the covering 23 on the interior surface of the central portion 21, increases the thickness of the central portion 21. This increased thickness of the central portion 21 provides some additional torques placed upon the left section 22L and the right section 22R when they are bent around the bridge of the nose and adhesively attached onto the sides of the nose. This increased torque is directly a result of the increased thickness of the central portion 21 of the nasal strip 20. This design provides the additional torque when the nasal strip 20 is bent around the bridge of the nose. This increased torque can provide increased openings of the left and right nasal passageways. Secondly, there is reduced discomfort upon removal of the improved design of the nasal strip 20 when it is taken off a person's nose. This is because the strongest adhesion of a nasal strip is at the center of the nose due to the fact there is typically less oil on that surface of the skin as compared to some oiliness that does typically occur at the side of a person's nose. Additionally, the fact that there is less of the skin of the nose that is covered with an adhesive automatically makes the improved nasal strip 20 removable with less discomfort. Thirdly, it is awkward to accurately place the nasal strip 10 onto the nose because it has an adhesive placed onto it entire interior surface. With the covering 23 as shown in FIGS. 3 and 4, it is much easier to hold onto the nasal strip 20 in a region where there is no adhesive, namely, the central portion 21 for more accurate placement of the nasal strip 20 onto the skin of the nose. Fourthly, to have less area of the skin on the nose that is covered with an adhesive dictates that any inflammatory skin response to that adhesive would be reduced.

In light of this analysis, it has been shown that the novel and useful nasal strip 20 as described herein would have superior characteristics as compared to a prior art nasal strip 10 that is now being marketed in many countries. It should also be understood that the present invention envisages a central portion that does not have an adhesive surface with only the end sections having those interior adhesive surfaces. This design can be accomplished without the plastic covering 23 as shown in FIGS. 3 and 4 as long as no adhesive covering is placed onto the central portion 21.

FIG. 5 shows the subject nasal strip or nasal dilator 20A with additional non-adhesive tabs 30 would be attached to outer boundaries 35L and/or 35R of the left section 32L and the right section 32R. The tabs(s) 30 may be attached to any part of boundaries 35L and 35R and may even be secured to central portion 21 to aid a user in removal of the nasal dilator 20 from the user's nose after application. For purposes of illustration, two tabs 30 are shown in FIG. 5 however it is to be understood that only one tab 30 may be used with relation to the subject nasal dilator 20A.

Tabs 30 may be formed of a flexible composition such as plastic or textile material which permits the user to grasp the tab 30 for aiding the user to readily remove the nasal dilator 20A from the user's nose with a minimal amount of discomfort. Still further, either or both tabs 30 may be formed integral with the left section 32L and/or the right section 32R.

The particular placement of tab 30 on the outer boundary 35L or 35R and/or the central portion 21 is not important to the inventive concept as long as the tab 30 extends external to the outer edges of the nasal dilator 20A anywhere along the directions 38 and 34 as noted in FIGS. 3 and 5.

In summary, as shown in FIGS. 3-5, nasal strip 20 or nasal dilator 20A each include a back portion or backing layer 21B of nasal strip 20 which is formed of a shape memory composition, well known in the art. The shape memory composition may be a plastic composition or of metallic composition which provides biasing forces to nasal dilator 20 or 20A to return dilator 20 or 20A to an original substantially planar contour after application of the nasal strip onto the nose of the user. In this manner, a force is applied to the outer tissue of the right and left nostril of a user to dilate the respective nasal passageways.

The backing layer 21 in its pre-applied mode of operation is substantially planar and extends in longitudinal direction 34 as seen in FIGS. 3 and 5. Backing layer 21B includes central section or portion 21, as well as opposing end sections 22L and 22R.

An adhesive coating layer 21A is formed on an interior surface of each of first and second opposing end sections 22L and 22R. A non-adhesive layer composed of a centrally located adhesive covering 21A and a flexible non-adhesive covering member 23 substantially covers the central portion 21 of nasal dilator 20.

Thus, the centrally located non-adhesive layer includes central adhesive layer 21A formed on an interior surface of central section 21 and sandwiched between the interior surface of central section 21 and the non-adhesive covering member 23 to provide a cushioning effect when nasal dilator 20 is applied to the bridge of the nose of a user. It is of importance that the combination of the cover member 23 and the adhesive covering 21A over the central portion increases the thickness of central section or portion 21 taken with respect to direction line 36 when compared to a thickness of end sections 22L and 22R. The increased overall thickness of central section 21 produces an increased torque or biasing force applied by end sections 22L and 22R when the nasal strip or dilator 20 is applied to opposing sides of the user's nose, thereby increasing the dilation of the user's nasal passageways, which is the general purpose and objective of nasal dilator 20.

To increase the overall biasing force applied to opposing sides of the user's nose, opposing end sections 22L and 22R have a width or thickness (taken with respect to directional line 38) greater than the width of the central portion 21 thereby increasing the adhesive surface area of end portions 22L and 22R which in turn increases the biasing return force applied to opposing sides of the user's nose.

Additionally, the combined adhesive surface areas of end sections 22L and 22R may be formed to provide a combined adhesive surface area greater than the area of central portion or section 21 thereby increasing the biasing force applied while minimizing any discomfort to the user when said dilator 20 or 20A is applied.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A nasal strip for opening the nasal passageways, the nasal strip having features that include:
   an external portion that extends for the entire length of the nasal strip, the external portion being formed from a flexible plastic material, the external portion have a central portion and a left end section and a right end section;
   the central portion having adhesive layer situated between the nasal strip's external portion and a plastic covering on the interior surface of the central portion of the nasal strip; and,
   an interior surface of the external portion having an adhesive coating that covers the interior surface of each end section of the external portion of the nasal strip with the central portion not having an adhesive coating on its interior surface, said central portion having an increased thickness portion of the nasal strip when compared to the thickness of the end sections of the nasal strip, the increased thickness of the central portion creating an increased torque to be exerted outwardly on the sides of the nose when the end sections are adhesively attached to each side of the nose, this increased torque causing increased openings of the left and right nasal passageways.

2. The nasal strip of claim 1 where the central portion of the nasal strip has a decreased width as compared to the width of the end sections of the nasal strip.

3. The nasal strip of claim 1 where there is an adhesive covering on all interior surfaces of the external portion of the nasal strip with the central portion of the nasal strip having a non-adhesive material covering the adhesive on that central portion of the nasal strip.

4. The nasal strip of claim 1 where the length of the nasal strip is approximately 6 cm.

5. The nasal strip of claim 1 where the width of the end sections of the nasal strip is approximately 2 cm.

6. The nasal strip of claim 1 where the length of the central portion of the nasal strip is approximately 2.5 cm.

\* \* \* \* \*